United States Patent [19]

Kampe et al.

[11] Patent Number: 4,999,352
[45] Date of Patent: Mar. 12, 1991

[54] 1-(1-ARYL-2-HYDROXYETHYL)-IMIDAZOLES AND SALTS THEREOF, MEDICAMENTS CONTAINING THESE COMPOUNDS, AND THE USE THEREOF

[75] Inventors: Klaus-Dieter Kampe, Bad Soden am Taunus; Patricia Usinger, Eppstein/Taunus; Herbert Siegel, Hofheim am Taunus; Hans G. Alpermann, Königstein/Taunus; Hermann J. Gerhards, Hofheim am Taunus, all of Fed. Rep. of Germany

[73] Assignee: Hoechst Aktiengesellschaft, Frankfurt, Fed. Rep. of Germany

[21] Appl. No.: 441,200

[22] Filed: Nov. 28, 1989

Related U.S. Application Data

[63] Continuation of Ser. No. 164,135, Mar. 4, 1988, abandoned.

[30] Foreign Application Priority Data

Mar. 6, 1987 [DE] Fed. Rep. of Germany ....... 3707151

[51] Int. Cl.⁵ .................. A61K 31/535; C07D 211/06; C07D 233/54; C07D 413/00
[52] U.S. Cl. ............................. 514/235.8; 548/341; 548/336; 544/139; 546/205; 546/210; 514/319; 514/326; 514/397; 514/399
[58] Field of Search ............... 548/341, 336; 544/139; 546/205, 210; 514/235.8, 319, 326, 397, 399

[56] References Cited

U.S. PATENT DOCUMENTS

| | | | |
|---|---|---|---|
| 3,796,704 | 3/1974 | Metzger et al. | 560/100 X |
| 3,897,438 | 7/1975 | Draber et al. | 548/341 |
| 4,243,405 | 1/1981 | Balasubramanyan et al. | 71/76 |
| 4,415,586 | 11/1983 | Kramer et al. | 548/341 |
| 4,472,415 | 9/1984 | Worthington et al. | 548/341 |
| 4,472,421 | 9/1984 | Buchel et al. | 548/341 |
| 4,505,922 | 3/1985 | Jager et al. | 548/341 |
| 4,578,396 | 3/1986 | Jager et al. | 548/341 |
| 4,582,843 | 4/1986 | Timmler et al. | 548/341 |
| 4,634,466 | 1/1987 | Noon et al. | 548/341 |
| 4,876,354 | 10/1989 | Siegel et al. | 548/341 |

FOREIGN PATENT DOCUMENTS

| | | | |
|---|---|---|---|
| 567100 | 12/1983 | Australia | 548/341 |
| 569135 | 7/1985 | Australia | 548/341 |
| 0025948 | 4/1981 | European Pat. Off. | 548/341 |
| 061835 | 10/1982 | European Pat. Off. | 548/341 |
| 0099165 | 1/1984 | European Pat. Off. | 548/341 |
| 0129798 | 1/1985 | European Pat. Off. | 548/341 |
| 0149976 | 7/1985 | European Pat. Off. | 548/341 |
| 0192055 | 8/1986 | European Pat. Off. | 548/341 |
| 2063857 | 12/1970 | Fed. Rep. of Germany | 548/341 |
| 2009020 | 11/1971 | Fed. Rep. of Germany | 548/341 |
| 2041771 | 2/1972 | Fed. Rep. of Germany | 548/341 |
| 2720868 | 11/1978 | Fed. Rep. of Germany | 548/341 |
| 2758784 | 7/1979 | Fed. Rep. of Germany | 548/341 |
| 0026856 | 4/1981 | Fed. Rep. of Germany | 548/341 |
| 2948206 | 6/1981 | Fed. Rep. of Germany | . |
| 3345813 | 6/1985 | Fed. Rep. of Germany | . |
| 3628545 | 4/1987 | Fed. Rep. of Germany | 548/341 |

OTHER PUBLICATIONS

So. African Patent Journal, Aug. 1986, pp. 129–130, G. Walther et al., abstract of So. African Patent No. 84/9745, 6/16/88.
M. Ogata et al., Chemistry and Industry, 19 (1980), pp. 85 and 86.
K. H. Buchel et al., Drugs Made in Germany, vol. 15, pp. 79–94 (1972).
Chemical Abstracts, 91, 57005p, 1979.

*Primary Examiner*—Mary C. Lee
*Assistant Examiner*—Robert C. Whittenbaugh
*Attorney, Agent, or Firm*—Finnegan, Henderson, Farabow, Garrett and Dunner

[57] ABSTRACT

1-(1-Aryl-2-hydroxyethyl)-imidazoles and salts thereof, processes for the preparation thereof, medicaments containing these compounds, and the use thereof.

The invention relates to 1-(1-aryl-2-hydroxyethyl)-imidazoles of the formula I

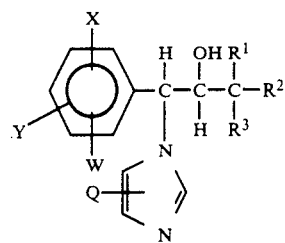

in which $R^1$, $R^2$, $R^3$, Q, W, X and Y have the meanings specified, and also to medicaments based on these compounds, in particular those having an antimycotic and an antidepressive action.

7 Claims, No Drawings

1-(1-ARYL-2-HYDROXYETHYL)-IMIDAZOLES AND SALTS THEREOF, MEDICAMENTS CONTAINING THESE COMPOUNDS, AND THE USE THEREOF

This application is a continuation of application Ser. No. 07/164,135, filed Mar. 4, 1988 now abandoned.

1-(1-Aryl-2-hydroxyethyl)-imidazoles and salts thereof, processes for the preparation thereof, medicaments containing these compounds, and the use thereof.

The invention relates to substituted 1-(1-aryl-2-hydroxy ethyl)-imidazoles, including their salts, processes for the preparation thereof, medicaments containing these compounds, and their use as medicaments.

It has already been proposed (cf. German Patent Application P 3,628,545.5) that substituted arylmethylazoles and salts thereof which are produced from the reaction of 1-(arylmethyl)-azoles with ketones and aldehydes be used for the treatment of depressive states as a consequence of their psychopharmacological action, in particular their antidepressive action.

The invention had the object of providing compounds which produce a therapeutically utilizable antidepressive action with good tolerance.

The substances proposed in German Patent Application P 3,628,545.5 have one or two asymmetrical carbon atoms. It has now been found that compounds having at least two asymmetrical carbon atoms produce, in particular, a good antidepressive action, besides an antimycotic action, simultaneously with good tolerance.

The invention therefore relates to 1-(1-aryl-2-hydroxyethyl)-imidazoles of the formula I,

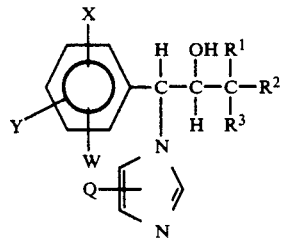

in which

X denotes H, $(C_1-C_4)$-alkyl, phenyl, F, Cl, Br, IOH, $CF_3$, $(C_1-C_4)$-alkoxy, $(C_1-C_4)$-alkylthio, $(C_1-C_4)$-alkoxy-methyl, $(C_3-C_5)$-alkenyloxymethyl or $-NR_2^4$, in which $R^4$ are identical or different and denote $(C_1-C_4)$-alkyl or, together with the nitrogen atom, a pyrrolidine, piperidine or morpholine radical, Y denotes H, $(C_1-C_4)$-alkyl, F, Cl, Br or $(C_1-C_4)$-alkoxy, or X and Y together in the 3,4-position denote a $-(CH_2)_L$-chain, where $L=3$ or 4, $-OCH_2CH_2-$, $-O-CH_2O-$ or $-CH=CH-CH=CH-$, W denotes H, $CH_3$ or $OCH_3$, $R^1$ denotes H, $(C_2-C_4)$-alkyl, $(C_2-C_5)$-alkenyl, $(C_2-C_5)$ alkynyl, $(C_3-C_8)$-cycloalkyl, $(C_4-C_8)$-cycloalkenyl, $(C_3-C_7)$-cycloalkyl-$CH_2$, $(C_4-C_7)$-1-cycloalkenyl-$CH_2$, $(C_1-C_4)$-alkoxy, $(C_1-C_4)$-alkoxymethyl, $(C_3-C_5)$-alkenyloxymethyl or 2-propyn-1-yloxymethyl,

[benzene ring]—$(C_1-C_3)$-alkyl or

[benzene ring]—$(CH=CH-CH_2)$ in which $R^5$ denotes $CH_3$, $C_2H_5$, $OCH_3$, F, Cl, Br or $CF_3$, and n denotes 0, 1 or 2 and, in the case where $R^5$ denotes $CF_3$, n is 1, $R^2$ denotes $(C_1-C_4)$-alkyl or $(C_3-C_5)$-alkenyl, $R^3$ denotes $(C_1-C_4)$-alkyl or $R^1$ and $R^3$ or $R^2$ and $R^3$, together with the carbon atom to which they are bound, denote $(C_3-C_7)$-cycloalkyl, $C_7$-bicycloalkyl, $(C_4-C_7)$-cycloalkenyl or $C_7$-bicycloalkenyl which is in each case unsubstituted or substituted by 1-3 $CH_3$ and/or $OCH_3$ and/or Cl and in which, in the cycloalkenyl and bicycloalkenyl radicals, the C=C double bond is not in the 1-position, or (oxa-$C_2$-$C_5$)-cycloalkyl, and denotes H or $CH_3$ or $C_2H_5$ in the 4- and/or 5-position, and the physiologically acceptable acid-addition salts thereof and the stereoisomers and optically active enantiomers thereof.

Preferred compounds of the formula I are those in which at least one of the substituents has the following meaning:

X denotes H, $(C_1-4)$-alkyl, phenyl, F, Cl, Br, I, OH, $CF_3$, $CH_3OCH_2$, $C_2H_6OCH_2$, $CH_2=CHCH_2OCH_2$, $(C_1-C_4)$-alkoxy, $3-N(CH_3)_2$ or $C-CF_3$, Y denotes H, $CH_3$, CL or $OCH_3$ or X and Y together in the 3,4-position denote a $-(CH_2)_4-$, $-O-CH_2-O-$ or $-CH=CH-CH=CH-$ chain, W denotes H, $R_1$ denotes $(C_2-C_4)$-alkyl, $(C_2-C_5)$-alkenyl, 2-propynyl-yl, $(C_3-C_6)$-cycloalkyl, $(C_1-C_4)$-alkoxymethyl, $(C_3-C_5)$-alkenyloxymethyl or 2-propyn-1-yloxymethyl,

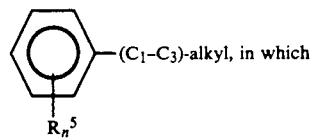

$R^5$ denotes $OCH_3$, F or Cl and n denotes 0 or 1, $R^2$ and $R^3$ denote $(C_1-C_4)$-alkyl or $R^1$ and $R^3$ or $R^2$ and $R^3$, together with the carbon atom to which they are bound, denote $(C_3-C_7)$-cycloalkyl, $C_7$-bicycloalkyl or $C_7$-bicycloalkenyl whose C=C double bond is not in the 1-position, each of which is unsubstituted or substituted by 1 or 2 $CH_3$ and/or $OCH_3$, or (oxa-$C_3$-$C_5$)-cycloalkyl, and Q denotes H or $CH_3$ in the 4- or 5-position.

Particularly preferred compounds of the formula I are those in which at least one of the substituents has the following meaning:

X denotes H, CH$_3$, phenyl, F, Cl, B4, 3- or 4-OCH$_3$ or 3-CF$_3$,

Y denotes H, CH$_3$, 3- or 4-Cl or 3- or 4-OCH$_3$, or

X and Y together in the 3,4-position denote a —CH=CH—CH=CH— chain,

W denotes H,

R$^1$ denotes (C$_2$–C$_4$)-alkyl, (C$_3$–C$_5$)-alkenyl, 2-propyn-1-yl, benzyl, (C$_1$–C$_4$)-alkoxymethyl or (C$_3$–C$_4$) alkenyloxymethyl, R$^2$ and R$^3$ denote (C$_1$–C$_4$)-alkyl or R$^1$ and R$^3$ or R$^2$ and R$^3$ together with the carbon atom to which they are bound, denote (C$_3$–C$_7$)-cycloalkyl, 2-norbornyl, norbornen-2-yl or (oxa-C$_3$–C$_5$)-cycloalkyl, and Q denotes H or CH$_3$ in the 4- or 5-position.

In this connection, the term "(C$_1$–C$_3$)-, C$_1$–C$_4$)- or (C$_2$–C$_4$)-alkyl" is in each case taken to mean an unbranched or branched alkyl radical, the term "(C$_2$–C$_5$)-, (C$_3$–C$_4$)- or (C$_3$–C$_5$)-alkenyl" or (C$_2$–C$_5$)-alkynyl is in each case taken to mean an unbranched or branched alkenyl or alkynyl radical respectively, the term "(C$_1$–C$_4$)- alkoxy or (C$_1$–C$_4$)alkylthio" is taken to mean an unbranched or branched alkoxy or alkylthio radical, the term (C$_3$–C$_8$)-cycloalkyl and (C$_4$–C$_8$)-cycloalkenyl is in each case taken to mean a saturated or unsaturated cyclic hydrocarbon radical having a total of 3–8 or 4–8 carbon atoms respectively, where these carbon atoms may be members of the ring or (C$_1$–C$_3$)-alkyl substituents, and the term C$_7$-bicycloalkyl or C$_7$-bicyclicalkenyl is taken to mean a saturated or unsaturated bicyclic ring system having 7 ring carbon atoms.

In the meanings mentioned for "R$^1$ and R$^3$ or R$^2$ and R$^3$ together", the terms (C$_3$–C$_7$)-cycloalkyl and (C$_4$–C$_7$)cycloalkenyl are taken to mean a saturated ring system comprising 3–7 carbon atoms or an unsaturated ring system comprising 4–7 carbon atoms, in each case including the carbon atom carrying the R$^1$ and R$^3$ or R$^2$ and R$^3$ radicals, and the terms C$_7$-bicycloalkyl and C$_7$-bicycloalkenyl are taken to mean a saturated or unsaturated respectively, bicyclic ring system comprising 7 ring carbon atoms, in each case including the carbon atom carrying the R$^1$ and R$^3$ or R$^2$ and R$^3$ radicals, the C=C double bond being present in one of the possible positions in the case of unsaturated ring systems.

The term (oxa-C$_2$–C$_5$)- or (oxa-C$_3$–C$_5$)-cycloalkyl is taken to mean a ring system which has 3 to 6 or 4 to 6 members respectively, including the carbon atom carrying the R$^1$ and R$^3$ or R$^2$ and R$^3$ radicals is substituted by R$^1$ or R$^2$ and comprises 2 to 5 or 3–5 carbon atoms respectively and an oxygen atom as a further ring member. Examples of these which may be mentioned are the oxetane, tetrahydrofuran and tetrahydropyran structure.

The compounds of the formula I contain at least two asymmetrical carbon atoms, to be precise those to which the imidazole radical and the hydroxyl group are bound. In addition, a third asymmetrical carbon atom is present if R$^1$, R$^2$ and R$^3$ are different or R$^1$ and R$^3$ or R$^2$ and R$^3$ together form an asymmetrical ring system. Further asymmetrical carbon atoms may be present in the R$^1$, R$^2$ and/or R$^3$ radicals. Consequently, the compounds I are produced in the synthesis at least as a racemate. Depending on the number of centers of asymmetry and depending on the degree of stereoselectivity under the conditions used, stereoisomers are produced, in addition, in the form of racemates. For example, in the synthesis of compounds of the formula I which contain two centers of asymmetry, two diastereomeric racemates can be formed in identical or different amounts. Such diastereomeric racemates are frequently produced in different amounts as a result of stereoselectivity, or only one is formed in the extreme case. The invention therefore also relates to the possible stereoisomers, in the simplest case the diastereomers, of the compounds I in the form of their racemates or in the form of the optically active enantiomers, and the pharmaceutically acceptable salts thereof.

The compounds of the formula I can be prepared, for example, by three processes.

It has already been proposed (cf. German Patent Application P 3,628,545.5) that 1-arylmethylazoles, after deprotonation using strong bases, be hydroxyalkylated at the methylene group using carbonyl compounds, strongly solvating solvents and/or two equivalents of this type of strong base being used. On the other hand, it was known from Org. React. 26, p. 128 (1979) that, in the reaction of 1-benzylimidazole with n-butyllithium in diethyl ether at temperatures between 0° C. and −70° C. and subsequent addition of carbonyl compounds, hydroxyalkylation occurs only at the 2-position of the imidazole ring.

It has furthermore been proposed (cf. German Patent Application P 3,628,545.5) that 2-aryl-2-(1-azolyl)-1-substituted ethanols be prepared by nucleophilically opening oxiranes of the formula IIa

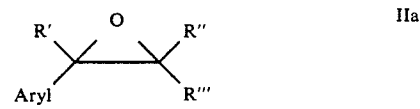

in which aryl, R', R" and R'" have the meanings mentioned in German Patent Application P 3,628,545.5 (there R'=R$^1$, R"=R$^3$ and R'"=R$^4$), using a compound of the formula IIIa

in which M denotes hydrogen or an alkali metal or an alkaline-earth metal, and Q and Z have the meaning specified in German Patent Application P 3,628,545.5, at a temperature between −20° C. and 150° C., preferably in a polar solvent, and then further reacting with a protonic acid.

The compounds of the formula I are now prepared analogously to these preparation processes proposed in German Patent Application P 3,628,545.5, in a process in which (A) one or up to two equivalents of a strong base are added to a 1-benzylimidazole of the formula IV

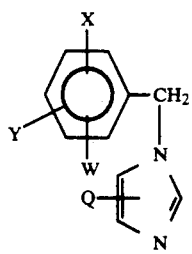

in which X, Y, W and Q have the abovementioned meanings, in an aprotic, expediently polar solvent at a temperature between +40° C., preferably 0° C., and −100° C., preferably −80° C., and the mixture is subsequently reacted initially with an aldehyde of the formula V

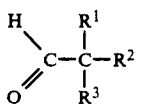

in which $R^1$, $R^2$ and $R^3$ have the abovementioned meanings, and then with a protonic acid, preferably with water, or (B) an oxirane of the formula II

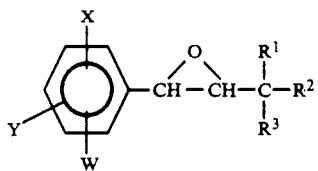

in which X, Y, W, $R^1$, $R^2$ and $R^3$ have the abovementioned meanings, is nucleophilically opened through reaction with a compound of the formula III

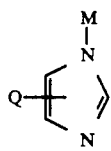

in which M denotes hydrogen or an alkali metal or alkaline-earth metal, and Q has the abovementioned meaning, at a temperature between −20° C., preferably 0° C., and 150° C., preferably 60° C., preferably in a polar solvent and a protonic acid is then added, or (C) in the case of compounds of the formula I which have been prepared by process (A) or (B), a substituent X and/or $R^1$ and/or $R^2$ is converted into another substituent X and/or $R^1$ and/or $R^2$ by known methods, and the compounds of the formula I obtained by processes (A), (B) and/or (C) are converted, if appropriate, into their physiologically acceptable acid-addition salts using inorganic or organic acids, and a compound obtained by (A), (B) or (C) is resolved, if appropriate, into its stereoisomers and/or its optically active enantiomers.

Suitable for the formation of acid-addition salts are all acids which form physiologically acceptable salts. These include inorganic acids and mono-, bi- and trifunctional organic acids, such as, for example, hydrochloric, hydrobromic or hydroiodic, sulfuric, phosphoric, nitric, benzenesulfonic, toluenesulfonic, sulfamic, methylsulfuric, acetic, propionic, oleic, palmitic, stearic, malonic, maleic, succinic, glutaric, malic, tartaric, citric, fumaric, lactic, glycolic, pyruvic, benzoic, toluic, glutamic, furancarboxylic, salicylic or mandelic acid. Preferred salts are those with physiologically acceptable inorganic acids, strong to medium-strong acidic derivatives of such acids or with succinic acid, L(+)-tartaric acid, D(−)-tartaric acid, malic acid, fumaric acid, (S)(+)-or (R)-(−)-mandelic acid.

Suitable strong bases in process (A) are, above all, alkali metal hydrides, such as, for example, sodium hydride, or alkaline-earth metal and alkali metal alkyls, such as, for example, n-butyllithium, tert.-butyllithium, methyllithium, phenyllithium or methylmagnesium chloride or bromide, or metallated amines, such as, for example, lithium diisopropylamide, potassium amide or sodium amide; lithium alkyls, such as n-butyllithium or lithium diisopropylamide, are preferably used.

The use of two equivalents of strong bases is appropriate in the majority of the substituents occurring according to the invention in the 1-benzylimidazoles to be used as starting materials, and also in such compounds of the formula IV which are unsubstituted in the benzyl radical. 1-Benzylimidazoles which are substituted in the phenyl radical by distinct acceptor substituents, such as, for example, $CF_3$, or which are substituted in the ortho and/or para-position by F, Cl and/or Br represent an exception to these. In these and in 1-(3-chlorophenylmethyl)imidazoles, the use of one equivalent of a strong base, preferably butyllithium, is sufficient to obtain adequately good yields of compounds of the formula I.

The reaction can be carried out in the solvents which are customary for organometallic reactions, such as, for example, dimethylformamide, dimethyl sulfoxide, dimethoxyethane, diethyl ether or, preferably, tetrahydrofuran. Mixtures of different aprotic solvents can also be used, including mixtures of polar and nonpolar solvents. In addition, additives such as N,N,N',N'-tetramethylethylenediamine or hexamethylphosphoric triamide can be used as solvents.

The reaction according to the invention with the strong base and the aldehyde of the formula V can be carried out at temperatures between +40° C. and −100° C., but preferably takes place in the range between 0° C. and −80° C. The reaction can also be carried out at a temperature above +40° C. The compounds of the formula I are isolated in the fashion which is conventional and known in organometallic reactions. The compounds of the formula I are generally purified by recrystallization from an organic solvent, such as, for example, hexane, cyclohexane, ethanol, ethyl acetate, diisopropyl ether or acetonitrile, or a mixture of solvent, or by column chromatography on silica gel.

The 1-benzylimidazoles of the formula IV which are unsubstituted or substituted according to the invention and used as starting material are obtained by known methods through alkylation of imidazole or imidazoles which are substituted in the 3- and/or 4-position using benzyl halides or using 2-chloro- or bromomethylnaphthalene.

The majority of the benzyl halides and chloro- or bromomethylnaphthalenes required as starting materials are known or can be prepared by known methods, for example by reaction of appropriate hydroxymethyl compounds with thionyl chloride or by bromination of appropriate methyl compounds using NBS (N-bromosuccinimide).

Some of the aldehydes of the formula V are known or can be prepared by known methods. For example, aldehydes having a tertiary formyl group can be synthesized by substitution of aldehydes of the formula VI

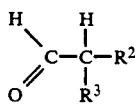

where $R^2$ and $R^3$ have the abovementioned meanings, in the α-position by suitable alkylating, alkenylating or alkynylating reagents of the formula $E-R^1$ in which $R^1$ has the abovementioned meanings and E denotes Cl, Br, I or one of the leaving groups which are conventionally used for such purposes, such as, for example, methanesulfonyloxy, benzene- or toluenesulfonyloxy. Such reactions may advantageously be carried out under the conditions of a phase-transfer reaction by allowing the reactants to act on one another in a suitable solvent, such as, for example, ether, dioxane, tetrahydrofuran, methylene chloride, tert.-butanol, an aliphatic, cycloaliphatic or aromatic hydrocarbon, such as hexane, cyclohexane, benzene, toluene or xylene, anisole or chlorobenzene, with vigorous stirring in the presence of a phase-transfer catalyst and either a powdered alkali metal hydroxide, such as, for example, sodium hydroxide or potassium hydroxide, or a concentrated aqueous solution thereof, preferably in a temperature range from 20° C. to 120° C.

Suitable phase-transfer catalysts are, for example, trialkylbenzylammonium or tetraalkylammonium halides, hydroxides or hydrogen sulfates preferably having 1 to 12 carbon atoms in the alkyl radical, or crown ethers, such as, for example, 12-crown-4, 15-crown-5, 18-crown-6 or dibenzo-18-crown-6.

On the other hand, aldehydes of the formula V can also be synthesized, for example, by mono- or dialkylating or-alkenylating aldehydes of the structure VII

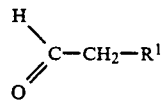

in the α-position in a fashion which is in principle similar to that described above.

Another way of preparing aldehydes of the formula V comprises oxidizing appropriate alcohols using methods which are known from the literature, for example using pyridinium chlorochromate (PCC). This method is used, inter alia, for the preparation of oxacycloalkane aldehydes, for example, from corresponding hydroxymethyl compounds.

In process (B), compounds of the formula III in which M denotes Li, Na or K, in particular Na, and Q denotes hydrogen or $CH_3$ are preferably used. The compounds of the formula III are known or can be prepared by known methods.

Oxiranes of the formula II are obtained by methods which are known from the literature. The olefin precursors are likewise prepared by known methods. The olefins are oxidized to the epoxide by methods which are known from the literature using an organic per-acid, such as, for example, peracetic acid or m-chloroperbenzoic acid.

In process (C), a substituent X and/or a substituent $R^1$ and/or a substituent $R^2$ in compounds of the formula I which have been prepared by processes (A) and/or (B) is converted into another substituent X and/or another substituent $R^1$ and/or another substituent $R^2$ by known methods.

For example, a benzyloxy radical in the phenyl group is converted into a hydroxyl group and toluene by catalytic hydrogenolysis by process (C), or a radical $R^1$ and/or a radical $R^2$ which in each case denote $(C_2-C_5)$- or $(C_3-C_5)$-alkenyl is converted into a $(C_2-C_5)$- or $(C_3-C_5)$-alkyl radical respectively by catalytic hydrogenation.

Suitable catalysts for this are in the first case, for example, various types of finely divided palladium on activated charcoal or on calcium carbonate or on barium sulfate, and in the second case, the hydrogenation of an alkenyl radical, various types of finely divided palladium, such as mentioned above for the first case, or finely divided platinum on activated charcoal or on aluminum oxide or platinum oxide.

The reaction times are several minutes to a few hours, depending on the process variant and depending on the temperature range.

The compounds of the formula I according to the invention contain two or more centers of asymmetry. Consequently, stereoisomeric mixtures are generally obtained in the synthesis. The individual stereoisomers can be produced here in different amounts as a result of different stereoselectivity. In the case of high stereoselectivity, for example, mainly or virtually exclusively only one diastereomer may be produced, as a racemate, in the case of diastereomers. Diastereomeric racemates and diastereomers in which, for example, a center of asymmetry is present in a unitary (R- or S-) configuration, of compounds of the formula I can be resolved in a conventional fashion, for example by selective, fractional crystallization or column chromatography.

The diastereomeric racemates can themselves be resolved into their optical antipodes (enantiomers) in a conventional fashion.

The racemates and diastereomeric racemates can be resolved by methods which are known in principle, for example by fractional crystallization of diastereomeric salts using optically active carboxylic acids or sulfonic acids of uniform configuration or by chromatography on chiral separating media (supports). Suitable optically active, chiral acids are, for example: L(+)- or D(−)-tartaric acid, D(+)- or L(−)-malic acid, R-(−)- or (S)-(+)-manelic acid, L(+)-lactic acid, (+)-camphor-10-sulfonic acid or (+)-3-bromocamphor-8-sulfonic acid. Diastereomeric salts of such chiral acids with compounds of the formula I are fractionally recrystallized from suitable solvents or mixtures of solvents until a constant rotation is achieved.

Through the action of an equivalent amount or an excess of base, the optically pure diastereomeric salts can be converted into the pure enantiomers of the compounds I and isolated as such.

If aldehydes of the formula V are used in the form of optically pure enantiomers in the synthesis of compounds I by process (A), it may occasionally be possible, if the crystallization tendency is sufficient, to resolve the diastereomers formed into the optical antipodes without a chiral auxiliary, for example a chiral acid, in a known fashion by fractional crystallization and/or by means of chromatographic methods.

It is possible to carry out the chromatographic resolution of diastereomers or racemates on chiral supports by means of conventional column chromatography, but more effective resolution is generally achieved using medium-pressure or high-performance liquid chromatography.

The compounds of the formula I and the acid-addition salts thereof are valuable medicaments. They are distinguished by a strong psychotropic action, in particular an antidepressive action, and can therefore be used for treating depressive states. They are active within a broad dose range. The level of the dose administered depends on the type of treatment desired, on the manner of administration, and on the condition, species and size of the mammal treated. In the case of oral dosage, satisfactory results are achieved using doses from 0.1 mg, preferably from 0.4 mg, up to 100 mg, preferably up to 20 mg, of a compound of the formula I per kg of body weight.

The compounds of the formula (I) and the acid-addition salts thereof represent valuable psychopharmaceuticals. They have a very good action in specific biochemical and pharmacological test models for antidepressives.

The compounds according to the invention antagonize tetrabenazine-induced ptosis in mice and rats with an orally administered $ED_{50}$ of 0.5–60 mg/kg. The appropriate amount of a homogenate of the respective substance in aqueous carboxymethyl cellulose is fed to six male animals using a stomach tube one hour before treatment with tetrabenazine (40 mg/kg intraperitoneally). Tetrabenazine induced ptosis is antagonized by this pretreatment.

The compounds I and the acid-addition salts thereof potentiate the toxicity of yohimbine in mice. At 0.5 to 100 mg/kg per os, type I antidepressives cause an increase in the death rate of an otherwise nonfatal dose of yohimbine hydrochloride (20 mg/kg administered subcutaneously).

An essential finding is that the compounds I and the salts thereof do not cause stereotypy in rats and mice after dosages in a therapeutically relevant range.

The antidepressive action and utility for the treatment of depressive states was furthermore demonstrated by means of the inhibition of reabsorption of noradrenalin in mouse brain synaptosoma preparations.

The compounds and the acid-addition salts thereof are particularly valuable through a structure differing from the antidepressives known hitherto. Their action is equal or superior to known commercial products and they have a lower toxicity.

In addition, the compounds of the formula I have an antimycotic action. They have a very good action in vitro against skin fungi, such as, for example, *Trichophyton mentagrophytes, Microsporum canis* and *Epidermophyton floccosum;* against mold fungi, such as, for example, *Aspergillus niger,* or against yeasts, such as, for example, *Candida albicans, C. tropicalis, Torulopsis glabrata* and *Trichosporon cutaneum,* and, in addition, against protozoa, such as *Trichomonas vaginalis* or *T. fetus, fetus,* and also against Gram-positive and Gram-negative bacteria.

There is likewise a very good effect against various pathogens of skin mycosis (for example *Trichophyton mentagrophytes*) in guinea pigs, in particular after local administration.

The present invention includes pharmaceutical preparations which, besides nontoxic, inert, pharmaceutically suitable excipients, contain one or more active ingredients according to the invention or comprise one or more active ingredients according to the invention, and processes for the preparation of these preparations.

Nontoxic, inert, pharmaceutically suitable excipients are taken to mean solid, semisolid or liquid diluents, fillers and formulation auxiliaries of all types.

Possible suitable forms of administration of the compounds according to the invention are, for example, tablets, coated tablets, capsules, pills, aqueous solutions, suspensions and emulsions, if appropriate sterile injectable solutions, nonaqueous emulsions, suspensions and solutions, ointments, creams, pastes, lotions, sprays etc.

The therapeutically active compounds should expediently be present in the abovementioned pharmaceutical preparations in a concentration of about 0.01, preferably 0.10, to 99.0, preferably 50.0, per cent by weight of the total mixture.

The administration concentrations for solutions, gels, creams or ointments and aerosols in the form of sprays are generally between 0.1–20, preferably 0.5–5, per cent by weight.

For local administration as antimycotics, suspensions, solutions, gels, creams, ointments or suppositories can be used, for example.

The abovementioned pharmaceutical preparations can also contain further pharmaceutical active ingredients in addition to the active ingredients according to the invention.

The abovementioned pharmaceutical preparations are prepared in a conventional fashion by known methods, for example by mixing the active ingredient or ingredients with the excipient or excipients.

The present invention also includes the use of the active ingredients according to the invention and pharmaceutical preparations which contain one or more active ingredients according to the invention in human and, in the case of antimycotically active compounds, in human and veterinary medicine for prevention, improvement and/or cure of the abovementioned disorders.

In the case of antimycotically acting compounds according to the invention, it has proven advantageous, both in human and in veterinary medicine, to administer the active ingredient or ingredients according to the invention in total amounts of about 0.05 to 200, preferably 0.1 to 100, in particular 0.5 to 30mg/kg of body weight per 24 hours, if appropriate in the form of several individual doses, in order to achieve the desired results. The total amount is administered in 1 to 8, preferably in 1 to 3, individual doses.

The active ingredients or the pharmaceutical preparations can be administered locally, parenterally, intraperitoneally and/or rectally.

The compounds of the present invention, and the salts thereof, which can be used as antidepressives can be used for the preparation of pharmaceutical preparations which contain an effective amount of the active substance together with excipients and which are suitable for enteral and parenteral administration. Tablets or gelatin capsules which contain the active ingredient together with diluents, for example lactose, dextrose, sucrose, mannitol, sorbitol, cellulose and/or glycine, and lubricants, such as siliceous earth, talc, stearic acid or salts thereof, such as magnesium stearate or calcium stearate, and/or polyethylene glycol, are preferably used. Tablets also contain binders, such as magnesium aluminum silicate, starch, gelatin, tragacanth, methylcellulose, sodium carboxymethylcellulose and/or polyvinylpyrrolidone and, if necessary, colorants, flavorings and sweeteners. Injectable solutions are preferably isotonic aqueous solutions or suspensions which can be sterilized and can contain auxiliaries, such as preservatives, stabilizers, wetting agents and/or emulsifiers, solubilizers, salts for regulation of osmotic pressure and/or buffer substances. The pharmaceutical preparations according to the invention, which may contain, if desired, pharmacologically useful substances, are prepared, for example, by means of conventional mixing/granulating and coating processes and contain 0.1% to about 75%, preferably about 1% to about 50%, of the active ingredient.

Oral administration is carried out in pharmaceutically conventional preparations, for example in the form of tablets, coated tablets or capsules, which contain, for example, 5, preferably 30, to 600 mg, preferably to 300 mg, of the active ingredient per daily dose mixed with a customary excipient and/or constituent, it being possible for individual doses of 5 to 200 mg to be administered, preferably once to three times daily.

However, it may be necessary to differ from the dosages mentioned, and in particular to do so as a function of the species and body weight of the object to be treated, the nature and severity of the disorder, the type of preparation and administration of the medicament and the period of time or interval within which administration takes place. Thus, it may in some cases be sufficient to manage with less than the abovementioned amount of active ingredient, whereas in other cases it is necessary to exceed the abovementioned amount of active ingredient. The optimum dosage and type of administration of the active ingredients necessary in each case can easily be determined by those skilled in the art on the basis of their expert knowledge.

The compounds of the formula I according to the invention are also fungicidally active. The range of action of the compounds claimed covers a large number of different phytopathogenic fungi, such as, for example, Piricularia oryzae, Pellicularia sasakii, various types of rust, Cercospora species and true mildew fungi in fruit, vegetable, cereal and ornamental plant growing.

The following examples illustrate the preparation of the compounds. The reactions described in the examples were carried out under a nitrogen atmosphere.

EXAMPLE 1

1-(1-Allyl-1-cyclohexyl)-2-(3-chlorophenyl)-2-(1-imidazolyl)-ethanol 13.6 ml (20.1 mmol) of a 1.48 molar solution of n-butyllithium in hexane were added dropwise to a solution of 3.85 g (20 mmol) of 1-(3-chlorobenzyl)-imidazole in 40 ml of absolute tetrahydrofuran (THF) at $-70°$ C. The mixture was stirred for a further 30 minutes at $-70°$ C., and a solution of 3.60 g of 85% purity (20 mmol) 1-allyl-1-formylcyclohexane in 30 ml of absolute tetrahydrofuran (THF) was then added dropwise at $-70°$ C. over about 20 minutes. The reaction mixture was subsequently stirred for a further 15 minutes at about $-70°$ C. and allowed to warm to room temperature over about 2 hours, 200 ml of water were added at about $5°$-$16°$ C. with cooling, the mixture was stirred for a further 45 minutes at about $5°$-$15°$ C., the phases were separated, and the aqueous phase was extracted repeatedly with ether. The combined organic solutions were washed with about 20 ml of water, dried, filtered and evaporated in vacuo. The extract residue (6.8 g) was dissolved in acetonitrile, after which crystalline 1-(1-allyl-1-cyclohexyl)-2-(3-chlorophenyl)-2-(1-imidazolyl)-ethanol (2.56 g) precipitated. The product (2.6 g) was recrystallized from 20 ml of acetonitrile. After this, 2.3 g of pure product (melting point 119° C.) were produced. After concentration of the mother liquors, a further 0.6 g of product were obtained which, after recrystallization from acetonitrile, gave a further 0.42 g of pure product (melting point 119° C.). The yield of pure 1-(1-allyl-1-cyclohexy)-2-(3 chlorophenyl)-2-(1-imidazolyl)-ethanol was 2.72 g ($\approx$39.4% of theory).

$C_{20}H_{25}ClN_2O$ (344.88) calculated: C 69.65 H 7.31 Cl 10.28 N 8.12% found: C 69.7 H 7.3 Cl 10.5 N 8.4%.

EXAMPLE 2

1-(3Chlorophenyl)-3,3-dimethyl-1-(1-imidazolyl)-5-hexen-2-ol 16.2 ml (25.1 mmol) of a 1.55 molar solution of n-butyllithium in hexane were added dropwise to a solution of 4.82 g (25 mmol) of 1-(3-chlorobenzyl)-imidazole in 50 ml of absolute THF at $-70°$ C. The mixture was stirred for a further 30 minutes at $-70°$ C., and a solution of 3.75 g of 75% purity (25 mmol) (containing 15% of toluene) 2,2-dimethyl-4-pentenaldehyde in 38 ml of absolute THF was then added dropwise at about $-70°$ C. over about 15 minutes. The reaction mixture was subsequently stirred for a further 15 minutes at about $-70°$ C. and allowed to warm to room temperature over about 2 hours, 350 ml of water were added at $1°$-$10°$ C. with cooling, the mixture was stirred for a further 30 minutes at $10°$-$20°$ C., the phases were separated, and the aqueous phase was extracted repeatedly with ether. The combined organic solutions were further worked up as described in Example 1. The extract residue (7.2 g) was chromatographed, eluting with $CH_2Cl_2$/hexane 1:2 and 1:1 mixtures, $CH_2Cl_2$ and $CH_2Cl_2/C_2H_5OH$ mixtures with an increasing $C_2H_5OH$ content (to a maximum of 2% by volume) on a silica gel S/$CH_2Cl_2$: hexane 1:2 column ($\phi$2.8 cm, height 43 cm).

After elution of 0.60 g preliminary fractions, 5.0 g of product, in which the compound desired was greatly concentrated, were eluted. From this proportion, 3.10 g ($\approx$40.7% yield) of pure 1-(3-chlorophenyl)-3,3-dimethyl1-(1-imidazolyl)-5-hexen-2-ol of melting point 95° C. were obtained by crystallization from diisopropyl ether $C_{17}H_{21}ClN_2O$ (304.83) calculated: C 66.98 H 6.94 Cl 11.63 N 9.19% found: C 67.4 H 7.1 Cl 12.0 N 9.2%.

EXAMPLE 3

1-(3Chlorophenyl)-3,3-dimethyl-1-(4(5)-methyl-1-imidazolyl)-5-hexen-2-ol 16.2 ml of 1.55 molar n-butyllithium/hexane solution and a solution of 3.75 g of 75% purity 2,2-dimethyl-4-pentenaldehyde in 38 ml of absolute THF were successively added dropwise, as described in Example 2, to a solution of 5.17 g (25 mmol) of 1-(3-chlorobenzyl)-4(5)-methylimidazole (6:4 mixture) in 50 ml of absolute THF at $-70°$ C. The further procedure was likewise carried out as described in Example 2. The extract residue (8.0 g) was chromatographed by elution with $CH_2Cl_2$ and $CH_2Cl_2/C_2H_5OH$ mixtures with an increasing $C_2H_5OH$ content (to a maximum of 2% by volume) on a silica gel S/CH$_2$Cl$_2$ column ($\phi$ 2.8 cm, height 46 cm). After elution of 0.63 g preliminary fractions, 0.75 g of impure product was eluted, from which 0.12 g of 1-(3-chlorophenyl)-3,3-dimethyl-1-(4(5)-methyl-1-imidazolyl)-5-hexen-2-ol (as a 4- and 5-methylimidazolyl mixture) were obtained in crystalline form from diisopropyl ether. 4.80 g of greatly concentrated product were then eluted, from which 3.45 g of crystalline product were obtained from diisopropyl ether. In total, 3.57 g ($\approx$44.8% yield) of pure 1-(3-chlorophenyl)-3,3-dimethyl-1-(4(5)-methyl1-imidazolyl)5-hexen-2-ol (as a 4- and 5-methyl mixture) of melting point 92° C. were obtained.

C$_{18}$H$_{23}$ClN$_2$O (318.86) calculated: C 67.80 H 7.27 Cl 11.12 N 8.79% found: C 68.1 H 7.4 Cl 11.3 N 8.5%.

EXAMPLE 4

1-(2-Allyl-5-norbornen-2-yl)-2-(3-chlorophenyl)-2-(1-imidazolyl)-ethanol 13.8 ml (20 mmol) of a 1.45 molar solution of n-butyllithium in hexane were added dropwise to a solution of 3.85 g (20 mmol) of 1-(3-chlorobenzyl)-imidazole in 40 ml of absolute THF at −70° C. After stirring for 30 minutes at −70° C., a solution of 4.39 g of 74% purity (20 mmol) 2-allyl-5-norbornen-2-aldehyde in 30 ml of absolute THF was added dropwise at about −70° C. over about 12 minutes. The further procedure was subsequently carried out as described in Example 2. The residue (9.0 g) remaining from the organic component after removing the solvent by distillation was dissolved in diisopropyl ether/hexane 2:1, whereupon crystalline product precipitated. After isolation using 20 ml of acetonitrile, this was boiled briefly, filtered off under suction after cooling the mixture, and washed with acetonitrile. 2.70 g ($\approx$38% yield) of pure 1-(2-allyl-5-norbornen-2-yl)-2-(3-chlorophenyl)-2-(1-imidazolyl)-ethanol were obtained in the form of a mixture, comprising 2 diastereomers, of melting point 134°-135° C.

C$_{21}$H$_{23}$ClN$_2$O (354.87) calculated: C 71.08 H 6.53 Cl 9.99 N 7.89% found: C 71.2 H 6.7 Cl 10.3 N 7.9%.

EXAMPLE 5

1-(4-Diphenyl)-3,3-dimethyl-1-(1-imidazolyl)-4-phenyl-2butanol 5.86 g (25 mmol) of 1-(4-diphenylmethyl)-imidazole in 50 ml of absolute THF were metallized at −70° C. as described in Example 2 using 16.2 ml of 1.55 molar n-butyllithium/hexane solution. A solution of 4.51 g of 90% purity 2,2-dimethyl3-phenylpropionaldehyde (25 mmol) in 35 ml of absolute THF was then added dropwise at −70° C., the mixture was stirred at −70° C. for 20 minutes and allowed to warm to room temperature over 2.5 hours, 250 ml of water were added dropwise at about 0° C., and the mixture was stirred for 1 hour with ice cooling. During this, a crystalline substance precipitated out; this was filtered off under suction, washed with water and ether and then dissolved in 100 ml of CH$_2$Cl$_2$/CH$_3$OH 1:1. After filtering, this solution was evaporated in vacuo, and the crystalline residue was boiled for 10 minutes with 35 ml of acetonitrile. After cooling to 5°-8° C., the solid was filtered off under suction and washed with acetonitrile. 2.70 g ($\approx$27.3% yield) of pure 1-(4-diphenyl)-3 3-dimethyl-1-(1-imidazolyl)-4-phenyl-2-butanol of melting point 220° C. were obtained.

C$_{27}$H$_{28}$N$_2$O (396.54) calculated: C 81.78 H 7.12 N 7.07% found: C 81.6 H 7.1 N 6.9%.

EXAMPLE 6

1-(3-Bromophenyl)-3,3-dimethyl-1-(1-imidazolyl)-5-hexen-2-ol

A solution of lithium diisopropylamide was prepared in 40 ml of absolute tetrahydrofuran (THF) at −30° C. starting from 2.06 g (20.4 mmol) of diisopropylamine and 13.4 ml of 1.5 molar n-butyllithium/hexane solution (20 mmol). A solution of 4.75 g (20 mmol) of 1-(3-bromobenzyl)imidazole in 25 ml of absolute THF was added dropwise to this solution at −70° C. to −78° C., the mixture was stirred at about −70° C. for a further 30 minutes, a solution of 3.22 g of 70% purity (20 mmol) 2,2-dimethyl-4-pentenaldehyde in 30 ml of absolute THF was subsequently added dropwise at about −70° C., and the mixture was stirred at about −70° C. for a further 20 minutes and allowed to warm to room temperature over about 2.5 hours 300 ml of water were subsequently added dropwise at 0° C.-5° C., and the mixture was stirred for 1 hour with ice cooling. After separating the phases, the aqueous solution was extracted repeatedly with ether. The combined organic solutions were further worked up as described in Example 1. The extract residue (7.3 g) was chromatographed by elution with CH$_2$Cl$_2$ and CH$_2$Cl$_2$/C$_2$H$_5$OH mixtures with an increase in C$_2$H$_5$OH content (to a maximum of 2% by volume) on a silica gel S/CH$_2$Cl$_2$ column ($\phi$ 2.8 cm, height 48 cm). After elution of 2.0 g preliminary fractions, 5.2 g of product were eluted in which the compound desired was greatly concentrated. From these 5.2 g, 3.05 g ($\phi$ 43.6% yield) of pure 1-(3-bromophenyl)-3,3-dimethyl-1-(1-imidazolyl)-5-hexen-2-ol of melting point 126° C. were obtained by crystallization from diisopropyl ether/hexane 2:1.

C$_{17}$H$_{21}$BrN$_2$O (349.29) calculated: C 58.46 H 6.06 Br 22.88 N 8.02% found: C 58.4 H 6.1 Br 23.8 N 8.0%.

The following compounds of the formula I were obtained analogously to Examples 1 to 6:

TABLE 1

| Ex. | X | Y | W | Q | R$^1$ | R$^2$ | R$^3$ | m.p. [°C.] |
|---|---|---|---|---|---|---|---|---|
| 7 | 3-Cl | H | H | H | CH$_2$—C=CH$_2$<br>$\|$<br>CH$_3$ | CH$_3$ | CH$_3$ | 102 |
| 8 | 3-Cl | 4-Cl | H | H | CH$_2$—CH=CH$_2$ | —(CH$_2$)$_5$— | | 143 |
| 9 | 3-Cl | H | H | H | CH$_2$C=CH$_2$<br>$\|$<br>CH$_3$ | C$_2$H$_5$ | C$_2$H$_5$ | -(oil) |
| 10 | 3-Cl | H | H | H | CH$_2$ | CH$_3$ | CH$_3$ | 151 |
| 11 | 3-Cl | H | H | H | CH$_2$— —Cl | CH$_3$ | CH$_3$ | 194 |
| 12 | 3-Cl | H | H | H | CH$_2$ | —(CH$_2$)$_5$— | | 188 |
| 13 | 4-C$_6$H$_5$ | H | H | H | CH$_2$—CH=CH$_2$ | CH$_3$ | CH$_3$ | 120 |

TABLE 1-continued

| Ex. | X | Y | W | Q | R¹ | R² | R³ | m.p. [°C.] |
|---|---|---|---|---|---|---|---|---|
| 14 | 4-C₆H₅ | H | H | H | CH₂—C(CH₃)=CH₂ | CH₃ | CH₃ | 140 |
| 15 | 3-F | H | H | H | CH₂—CH=CH₂ | CH₃ | CH₃ | 99 |
| 16 | 3-Cl | H | H | H | CH₂—CH=CH | CH₃ | CH₃ | 217 |
| 17 | 3-Cl | H | H | H | CH₂OCH₂CH₃ | CH₃ | CH₃ | 93 |

EXAMPLE 18

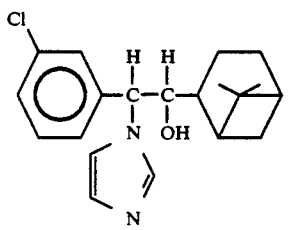

1-(6,6-Dimethylbicyclo[3,1,1]hept-2-yl)-2-(3-chlorophenyl)-2-(1-imidazolyl)-ethanol As described in Example 2, 770 g (40 mmol) of 1-(3-chlorobenzyl)-imidazole in 80 ml of absolute THF were metallized at −70° C. using 27 ml of 1.48 molar n-butyllithium/hexane solution. A solution of 6.10 g (40 mmol) of 2-formyl6,6-dimethylbicyclo[3,1,1]heptane(myrtanal) in 60 ml of absolute THF was then added dropwise at −70° C., and the mixture was stirred at −70° C. for 20 minutes and allowed to warm to room temperature over 2.5 hours. The further procedure was carried out analogously to that described in Example 2. The residue (13.60 g) remaining after evaporating the combined organic solutions (extracts) was chromatographed by elution with $CH_2Cl_2$ and $CH_2Cl_2/C_2H_5OH$ mixtures with an increasing $C_2H_5OH$ content (to a maximum of 3% by volume) on a silica gel S/$CH_2Cl_2$ column ($\phi$ 2.1 cm, height 62.5 cm). After elution of 4.7 g preliminary fractions and 2.4 g of product contaminated by by-products, 6.4 g of product were eluted in which the compound desired was present virtually pure in the form of stereoisomers. 1.52 g of a stereoisomer of 1-(6,6-dimethyl-bicyclo[3,1,1]hept-2-yl)-2-(3-chlorophenyl)-2-(1-imid-azolyl)-ethanol of melting point 149°–150° C. which was pure according to TLC and the ¹H NMR spectrum were obtained from this fraction by crystallization from diisopropyl ether.

The yield was 4.88 g (≈35.4% of theory) of stereoisomeric mixture and 1.52 g (≈11% of theory) of a pure, crystalline stereoisomer.

$C_{20}H_{25}ClN_2O$ (344.88) calculated: C 69.65 H 7.31 Cl 10.28 N 8.12% found: C 69.6 H 7.2 Cl 10.6 N 8.3% (stereoisomeric mixture) found: C 70.0 H 7.0 N 8.0% (pure diastereomer).

EXAMPLE 19

3,3-Dimethyl-1-(1-imidazolyl)-1-phenyl-5-hexen-2-ol 40 ml of 1.5 molar n-butyllithium/hexane solution were added dropwise to a solution of 4.75 g (30 mmol) of 1-benzylimidazole and 3.49 g (30 mmol) of N,N,N',N'-tetramethylethylenediamine (TMED(A) in 60 ml of absolute THF at −70° C. The mixture was stirred at −70° C. to −78° C. for a further 30 minutes, a solution of 3.74 g of 90% purity (30 mmol) 2,2-dimethyl-4-pentenaldehyde in 38 ml of absolute THF was then added dropwise at about −70° C. over 25 minutes, and the mixture was stirred at about −70° C. for a further 20 minutes and allowed to warm to room temperature over about 2 hours. 350 ml of water were then added at 0°–8° C., the mixture was stirred for a further 30 minutes while cooling in an ice bath, and the phases were subsequently separated and the aqueous solution was extracted repeatedly with ether. The combined organic solutions were further worked up as described in Example 1. The extract residue (8.4 g) was chromatographed, eluting with $CH_2Cl_2$ and $CH_2Cl_2/C_2H_5OH$ mixtures with an increasing $C_2H_5OH$ content (to a maximum of 2% by volume) on a silica gel S/$CH_2Cl_2$ column (2.8 cm, height 48 cm). After elution of 4.8 g preliminary fractions, 3.5 g of product were eluted in which the compound desired was contained. This product (3.5 g) was again chromatographed in the same fashion as described above on a silica gel S/$CH_2Cl_2$ column ($\phi$ 2.0 cm, height 60 cm), during which the composition of the fractions eluted was checked by thinlayer chromatography (TLC). After elution of 0.35 g preliminary fractions, 4 fractions were eluted (with $CH_2Cl_2/C_2H_5OH$ 99.6:0.4–99.5:0.5) which contained the compound desired in virtually pure form. These fractions were combined and evaporated in a high vacuum at a bath temperature of 65° C. until the weight remained constant. 0.62 g (≈7.6% yield) of 3,3-dimethyl-1-(1-imidazolyl)-1-phenyl-5-hexen-2-ol was thus obtained as a viscous, colorless oil; the ¹H NMR spectrum confirmed the structure of this compound.

$C_{17}H_{22}N_2O$ (270.38) calculated: C 75.52 H 8.20 N 10.36% found: C 74.9 H 8.3 N 10.1%.

The compound was present in further chromatography fractions, besides various amounts of by-products, so that the amount formed is well above the proportion specified above and isolated in virtually pure form.

EXAMPLE 20

3,3-Dimethyl-1-(1-imidazolyl)-1-(3-methoxyphenyl)-5-hexen-2-ol 7.52 g (40 mmol) of 1-(3-methoxybenzyl)-imidazole and 4.65 g (40 mmol) of TMEDA in 80 ml of absolute THF were metallized using 53.5 ml of 1.5 molar n-butyllithium/hexane solution according to the procedure described in Example 19, and the product was reacted with 5.00 g of 90% purity (≈40 mmol) 2,2-dimethyl-4-pentenaldehyde. Work-up was effected analogously to that in Example 19. The extract residue (12.2 g) was chromatographed as described in Example 19 on a silica gel S/$CH_2Cl_2$ column ($\phi$ 3.5 cm, height 40 cm), and the combined fractions which contained the compound desired (amount 6.3 g) were subsequently chromatographed a second time on a silica gel S/$CH_2Cl_2$ column ($\phi$ 2.4 cm, height 88 cm). A group of fractions (2.5 g) from the second chromatography crystallized from a hexane/diisopropyl ether 3:1 solution. After isolation of the substance, 0.77 g (≈6.3% yield) of pure 3,3-dimethyl-1-(1-imidazolyl)-1-(3-methoxyphenyl)5-hexen-2-ol of melting point 83° C. were obtained. $C_{18}H_{24}N_2O_2$ (300.41) calculated: C 71.97 H 8.05 N 9.33% found: C 68.9 H 8.0 N 8.6%.

EXAMPLE 21

3,3-Dimethyl-1-(3-fluorophenyl)-1-(4(5)-methyl-1-imidazolyl)-5-hexen-2-ol

A solution of 4.76 g (25 mmol) of 1-(3-fluorobenzyl)-4(5)-methylimidazole (3:2 mixture) and 2.91 g (25 mmol) of TMEDA in 50 ml of absolute THF was lithiated as described in Example 19 using 33.4 ml of 1.5 molar n-butyllithium/hexane solution. A solution of 3.11 g of 90% purity (25 mmol) 2,2-dimethyl-4-pentenaldehyde in 25 ml of absolute THF was then added dropwise at −70° C., and the mixture was stirred at about −70° C. for a further 20 minutes and allowed to warm to room temperature over about 2.5 hours. Work-up was subsequently effected as described in Example 19. The extract residue (7.6 g) was chromatographed as described in Example 19, on a silica gel $S/CH_2Cl_2$ column (2.8 cm, height 48 cm). After elution of 1.35 g preliminary fractions, 4.10 g of product in which the compounds desired were concentrated were eluted in the form of 10 fractions. A crystalline substance which after isolation and drying, gave 2.44 g (≈32.3% yield) of pure 3,3-dimethyl-1-(3-fluorophenyl)-1-(4(5)-methyl-1-imidazolyl)-5-hexen-2-ol (6.7:3.3 mixture of 4- and 5-methylimidazole compound) of melting point 118° C. was obtained from this product after dissolving in diethyl ether/hexane.

$C_{18}H_{23}FN_2O$ (302.40) calculated: C 71.49 H 7.67 F 6.28 N 9.26% found: C 71.3 H 7.8 F 6.3 N 9.2%

EXAMPLE 22

1 3,3-Dimethyl-1-(3-methoxyphenyl)-1-(4(5)-methyl-1-imidazolyl)-5-hexen-2-ol

A solution of 8.08 g (40 mmol) of 1-(3-methoxybenzyl)4(5)-methylimidazole (3:2 mixture) and 4.65 g (40 mmol) of TMEDA in 80 ml of absolute THF are lithiated as described in Example 19 using 53.5 ml of 1.5 molar n-butyllithium/hexane solution. A solution of 6.42 g of 70% purity (40 mmol) 2,2-dimethyl-4-pentenaldehyde in 50 ml of absolute THF was then added dropwise at −70° C., and the mixture was then stirred to about −70° C. for 20 minutes and allowed to warm to room temperature over the course of about 2.5 hours. Work-up was subsequently effected as described in Example 19. The extract residue (14 g) was chromatographed as described in Example 19 on a silica gel $S/CH_2Cl_2$ column (0 2.1 cm, height 67 cm). After elution of 4.4 g of preliminary fractions, 4.5 g of product in which the compounds desired were concentrated were eluted in the form of 3 groups of fractions. From these fractions, 0.56 g of pure crystalline 3,3-dimethyl-1-(3-methoxyphenyl)-1-(5(4)-methyl-1-imidazolyl)-5-hexen2-ol, melting point 119°-121° C. (5-methyl:4-methyl 87:13 according to the $^1H$ NMR spectrum) were obtained from diethyl ether/hexane. The oily lye residue (3.9 g) was again chromatographed in the same way. From a group of fractions (residue 1.8 g) containing the desired compounds in concentrated form, a further 0.60 g of crystalline product, melting point 125°-126° C. (5-methyl: 4-methyl compound about 9:1) was obtained.

$C_{19}H_{26}N_2O_2$(314.43) calculated: C 72.58 H 8.34 N 8.91% found: C 73.0 H 8.4 N 9.0%.

EXAMPLE 23

1-(3-Chlorophenyl)-3,3-dimethyl-1-(4-methyl-1-imidazolyl)-5-hexen-2-ol and
1-(3-chlorophenyl)-3,3-dimethyl-1-(5-methyl-1-imidazolyl)-5-hexen-2-ol A solution of 10.34 g (50 mmol) of 1-(3-chlorobenzyl)4(5)methylimidazole (3:2 mixture) in 100 ml of absolute THF was lithiated as described in Example 2 using 33.4 ml of 1.5 molar n-butyllithium/hexane solution. A solution of 6.24 g of 90% purity (50 mmol) 2,2-dimethyl-4-pentenal in 75 ml of absolute THF was then added dropwise at −70° C., and the mixture was stirred at about −70° C. for a further 40 minutes and allowed to warm to room temperature over the course of about 2.5 hours. Work-up was subsequently effected as described in Example 2. 1.5 g of crystalline product (melting point 136°-137° C.) (1-(3-chlorophenyl)-3,3-dimethyl-1-(5(4)-methyl-1-imidazolyl)-5-hexen-2-ol according to the $^1H$ NMR; 5-methyl:4-methyl compound 86:14) were obtained in addition to 11.6 g of oily ether extract residue. The latter was chromatographed as described in Example 19 (column: φ 2.6 cm, height 95 cm). After 1.8 g preliminary fractions, groups of fractions were obtained which, according to TLC and $^1H$ NMR, contain the desired compounds in concentrated form (5.8 g). From these groups of fractions, crystalline product was obtained, in each case from diethyl ether/hexane solutions. 1.35 g of crystals (4-methyl:5-methyl compound 75:25) were obtained from the first-eluted group of fractions (2.33 g), and 0.94 g of crystals (5-methyl:4-methyl compound about 1:1) from the subsequently eluted group 0.46 g of crystals, pure 1-(3-chlorophenyl)-3,3-dimethyl-1-(5-methyl1-imidazolyl)-5-hexen-2-ol, according to $^1H$ NMR melting point 142°-143° C., was obtained from the final group of fractions (2.93 g).

$C_{18}H_{23}ClN_2O$(318.86) calculated: C 67.80 H 7.27 Cl 11.12 N 8.79% found: C 67.5 H 7.3 Cl 11.0 N 9.0%.

The 0.94 g of product (5-methyl:4-methyl compound about 1:1) was recrystallized from ethyl acetate/diethyl ether/ diisopropyl ether. On doing this, 0.42 g of crystals with a 62% proportion of 5-methyl compound was obtained. The residue from the mother liquors (75% of 4- methyl compound) (0.5 g) was combined with the 1.35 g of product (75% of 4-methyl compound) obtained above, and this component was recrystallized as described above. From this procedure, 0.31 g of pure 1-(3-chlorophenyl)- 3,3-dimethyl1-(4-methyl-1-imidazolyl)-5-hexen-2-ol, according to 1H NMR, melting point 126°-127° C., was obtained.

$C_{18}H_{23}ClN_2O$(318.86) found: C 67.6 $H_{7.2}$ Cl 11.0 N 8.9%.

The 4-methyl- and 5-methyl-1-imidazolyl compounds differ, inter alia, clearly in the position of the $^1H$ NMR signal for the proton in the 2-position of the imidazole radical (measured in $CDCl_3$ using TMS as the internal standard) This signal is at 7.49 δ in the case of the 4-methyl-1imidazolyl compound, and, in contrast, at 8.16 δ in the case of the 5-methyl-1-imidazolyl compound.

EXAMPLE 24

3,3-Dimethyl-1-(4-diphenyl)-1-(4-methyl-1-imidazolyl)-5-hexen-2-ol 25 mmol of 1-(4-diphenylmethyl)-4(5)-methylimidazole in 50 ml of absolute THF were lithiated as described in Example 2 using 25 mmol of n-butyllithium, dissolved in hexane (1.5 molar). As described in Example 23, a solution of 3.12 g of 90% purity (25 mmol) 2,2-dimethyl4-pentenal in 35 ml of absolute THF was then added dropwise. Further treatment took place analogously to Example 23 or Example 19. 9.0 g of a viscous oil were obtained as the residue from the ether extract and were chromatographed as described in Example 19 (column: 2.8 cm, height 38 cm). After elution of 2.2 g preliminary fractions, 9 fractions (6.10 g) were eluted which contained the desired compounds (4- and 5-methylimidazolyl compounds) in highly concentrated form. Some of this product crystallized from acetonitrile. After isolation, 0.81 g of, according to $^1$H NMR, pure 3,3-dimethyl-14-diphenyl)-1-(4-methyl-1-imidazolyl)-5-hexen-2-ol, melting point 159°–160° C., was obtained.

$C_{24}H_{28}N_2O$(360.50) calculated: C 79.96 H 7.83 N 7.77% found C 80.1 H 8.1 N 7.6%.

EXAMPLE 25

2-(3-chlorophenyl)-2-(1-imidazolyl)-1-(3-methyl-3-oxetanyl)ethanol

A solution of 3.85 g (20 mmol) of 1-(3-chlorobenzyl)imidazole in 40 ml of absolute THF were lithiated as described in Example 2 using 14.7 ml of 1.5 molar n-butyllithium/hexane solution. A solution of 2.10 g (21 mmol) of 3-methyloxetan-3-aldehyde (see below) in 25 ml of absolute THF was then added dropwise over the course of about 30 minutes at −70° C., and the mixture was stirred at about −70° C. for a further 30 minutes and allowed to warm to room temperature over the course of about 3 hours. The mixture was subsequently cooled to −10° C., 200 ml of water were added dropwise, and the mixture was stirred for a further 30 minutes while cooling in an ice bath. The phases were then separated and the aqueous phase was extracted three times with ether. After drying, filtration and evaporation of the solvents, the combined organic phases gave 5.10 g of an oily residue, some of which crystallized from acetonitrile. Isolation of the crystalline substance gave 0.50 g of pure 2-(3-chlorophenyl)-2-(1-imidazolyl)-1-(3-methyl-3-oxetanyl)ethanol, melting point 228°–229° C., diastereomer A, (≈8.5% yield).

H $C_{15}H_{17}ClN_2O_2$(292.77) calculated: C 61.54 H 5.85 Cl 12.11 N 9.57% found: C 61.8 H 6.0 Cl 11.7 N 9.5%.

The residue from the mother liquors (4.6 g) was chromatographed as described in Example 19 on a silica gel S/$CH_2Cl_2$ column (2.8 cm, height 28 cm) ($CH_2Cl_2$/$C_2H_5OH$ mixtures with an increasing $C_2H_5OH$ content, to a maximum of 5% by volume). After elution of 1.10 g of preliminary fractions, 1.20 g of product were eluted, from which 0.37 g of the desired compound, diastereomer B, melting point 145°–146° C., crystallized out from a solution in acetonitrile. A further four subsequent fractions contained 1.5 g as eluate residue, which gave 0.96 g of 2-(3-chlorophenyl)-2-(1-imidazolyl)-1-(3-methyl-3-oxetanyl)-ethanol, diastereomer B, melting point 145°–146° C., from acetonitrile solution. In total 1.33 g of diastereomer B were isolated in crystalline form (melting point 145°–146° C.) (≈22.7% yield)

$C_{15}H_{17}ClN_2O_2$(292.77) calculated: C 61.54 H 5.85 Cl 12.11 N 9.57% found: C 61.8 H 5.6 Cl 12.4 N 9.5%

Preparation of 3-methyloxetan-3-aldehyde (starting material for the compounds of Example 25):

9.84 g (120 mmol) of powdered anhydrous sodium acetate were added to a solution of 37.05 g (172 mmol) of pyridinium chlorochromate in 300 ml of $CH_2Cl_2$. A solution of 12.27 g (120 mmol) of 3-methyl-3-hydroxymethyloxetane was added dropwise to this mixture over the course of 30 minutes at 7°–10° C. while stirring. The mixture was stirred for a further 3 hours at 8°–12° C. The reaction mixture was then poured into 900 ml of pentane, a viscous, dark resinous material depositing. After pouring off the pentane solution, this material was worked thoroughly several times with pentane. The pentane components were clarified through a filtration aid, washed by shaking once with saturated $NaHCO_3$/$H_2O$ solution, dried over $MgSO_4$ and, after filtration, concentrated on a 40 cm Vigreux column at a bath temperature of 50°–60° C. The residue was subjected to fractional distillation, initially at atmospheric pressure then under reduced pressure. A fraction (4.10 g ≈34% yield) of boiling point 117°–122° C. at 200 mbar was about 90% purity 3-methyloxetan-3-aldehyde according to the $^1$H NMR spectrum and was used in this form for the synthesis described in Example 25.

EXAMPLE 26

1-(4-Diphenyl)-3,3-dimethyl-1-(1-imidazolyl)-2-hexanol 170 mg of 5% platinum on activated charcoal was added as catalyst to a solution of 1.733 g (5 mmol) of 1-(4-diphenyl)3,3-dimethyl-1-(1-imidazolyl)-5-hexen-2-ol (compound according to Example 16) in 80 ml of methanol and mixed vigorously under a hydrogen atmosphere at a slight excess pressure of hydrogen at 24° C. and an atmospheric pressure of 984 mbar. After 1 hour, 120 ml of hydrogen had been taken up. The suspension was filtered under suction through a filtration aid and the filtrate was subsequently evaporated in vacuo. The crystalline residue remaining 1.75 g) was boiled briefly with 8 ml of diisopropyl ether, cooled in an ice bath, filtered off under suction and dried 1.63 g (≈93.7% yield) of pure 1-(4-diphenyl)-3,3-dimethyl1-(1-imidazoly)-2-hexanol of melting point 177° C. were obtained.

$CH_{23}H_{28}N_2O$ (348.49) calculated: C 79.27 H 8.10 N 8.04% found: C 78.5 H 8.1 N 7.9%

EXAMPLE 27

1-(3-chlorophenyl)-3,3-dimethyl-1-(1-imidazolyl)-2-hexanol

In the same fashion as described in Example 26, 1.43 g of 1-(3-chlorophenyl)-3,3-dimethyl-1-(1-imidazolyl)-2-hexanol of melting point 97° C. were obtained through hydrogenation on a 5 mmol scale of 1-(3-chlorophenyl)-3,3-dimethyl-1-(1-imidazolyl)-5-hexen-2-ol (compound according to Example 2) with 200 mg of sulfidized 5% platinum on activated charcoal as catalyst.

$C_{17}H_{23}ClN_2O$ (306.84) calculated: C 66.54 H 7.56 Cl 11.56 N 9.13% found: C 66.3 H 7.4 Cl 11.7 N 9.0%

EXAMPLE 28

1-(3-chlorophenyl)-3,3-dimethyl-1-(4-methyl-1-imidazolyl)-2-hexanol

In the same fashion as described in Example 26 through hydrogenation of 1.27 g (4 mmol) of 1-(3-chlorophenyl)-3,3-dimethyl-1-(4-methyl-1-imidazolyl)-5-hexen-2-ol (compound of Example 23) in 70 ml of methanol using 180 mg of sulfidized 5% platinum on activated charcoal as catalyst, 1.27 g of 1-(3-chlorophenyl)-3,3-dimethyl-1-(4-methyl-1-imidazolyl)-2-hexanol, melting point 121°–122° C., were obtained.

$C_{18}H_{25}ClN_2O$ (320.87) calculated: C 67.38 H 7.85 Cl 11.05 N 8.73% found: C 67.2 H 8.0 Cl 11.1 N 8.8%.

PHARMACOLOGICAL TEST

Test for influence on tetrabenazine-induced ptosis

Method

Male mice (SPF-71, KF:NMRI) weighing 18–22 g were allotted at random to treatment groups of 6 animals. The test substances were suspended in 1% strength methylhydroxyethylcellulose (MH)/water and administered orally at 10 ml/kg of body weight. A control group was given the solvent (1% strength MH), and the standard group was given 10 mg/kg p.o. of nomifensine (in 1% strength MH). The tetrabenazine solution used was prepared from methanesulfonate ($\approx$76.8% of base), and an amount corresponding to 40 mg/kg of tetrabenazine base was administered intraperitoneally 30 minutes after the test substances. The ptosis was assessed according to the following scale 30 minutes after administration of tetrabenazine:

| Ptosis | Score |
| --- | --- |
| Eyes closed | 4 |
| Eyes ¾ closed | 3 |
| Eyes ½ closed | 2 |
| Eyes ¼ closed | 1 |
| Eyes open | 0 |

The ptosis scores were cumulated and the result of the groups related to the maximum score achievable (6 × $\alpha$ = 100%). By means of linear regression, the $ED_{50}$ (mg/kg) was determined as the dose at which the degree of ptosis is 50% of the value determined in the control group. The following results were obtained:

| Compound according to example | $ED_{50}$ (confidence limit 95% mg/kg p.o. |
| --- | --- |
| 2 | 2.0 (0.5–8.8) |
| 13 | 1.3 (0.1–26.8) |
| 10 | 4.6 (2.2–9.7) |
| 1 | 3.9 (2.1–7.3) |
| 26 | 1.2 (0.3–5.4) |
| Standard nomifensine | 1.2 (0.7–2.0) |

The substance mentioned exhibited a strong action in the model of tetrabenazine-induced ptosis in mice, which applies as predictive for an antidepressive action in humans.

We claim:

1. 1-(1-Aryl-2-hydroxyethyl)-imidazole of the formula I

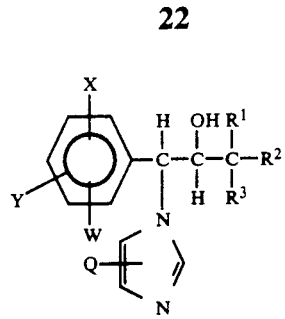

in which

X is H, $(C_1-C_4)$-alkyl, phenyl, F, Cl, Br, I, $CF_3$, $(C_1-C_4)$-alkoxy, $(C_1-C_4)$-alkylthio, $(C_1-C_4)$-alkoxymethyl, $(C_3-C_5)$-alkenyloxymethyl or $-NR_2^4$, in which the radicals $R^4$ are identical or different and are $(C_1-C_4)$-alkyl or, together with the nitrogen atom, a pyrrolidine, piperidine or morpholine radical, Y is H, $(C_1-C_4)$-alkyl, F, Cl, Br or $((C_1-C_4)$-alkoxy, or X and Y together in the 3,4-position represent a $-(CH_2)_L$-chain, where L=3 or 4, $-OCH_2CH_2-$, $-O-CH_2O-$ or $-CH=CH-CH=CH-$, W is H, $CH_3$ or $OCH_3$, $R^1$ is H, $(C_2-C_4)$-alkyl, $(C_2-C_5)$-alkenyl, $(C_2-C_5)$-alkynyl, $(C_3-C_8)$-cycloalkyl, $(C_4-C_8)$-cycloalkenyl, $(C_3-C_7)$-cycloalkyl$-CH_2$, $(C_4-C_7)$-1-cycloalkenyl-$CH_2$, $(C_1-C_4)$-alkoxymethyl, $(C_3-C_5)$-alkenyloxymethyl or 2-propyn-1-yloxymethyl,

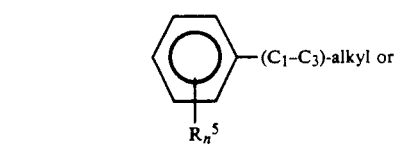

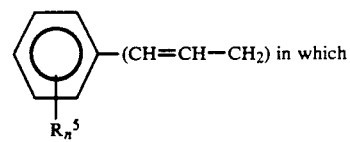

$R^5$ is $CH_3$, $C_2H_5$, $OCH_3$, F, Cl, Br or $CF_3$, and n is 0, 1, or 2 and, in the case where $R^5$ is $CF_3$, n is 1, $R^2$ is $(C_1-C_4)$-alkyl or $(C_3-C_5)$-alkenyl, $R^3$ is $(C_1-C_4)$-alkyl or $R^1$ and $R^3$ or $R^2$ and $R^3$, together with the carbon atom to which they are bound are $(C_3-C_7)$-cycloalkyl, $C_7$-bicycloalkyl, $(C_4-C_7)$-cycloalkenyl or $C_7$-bicycloalkenyl which is in each case unsubstituted or substituted by 1–3 $CH_3$ and/or $OCH_3$ and/or Cl and in which, in cycloalkyl and bicycloalkenyl radicals, the C=C double bond is in other than the 1-position, or (oxa-$C_2-C_5$)-cycloalkyl, and Q is H or $CH_3$ or $C_2H_5$ in the 4- and/or 5-position, or the physiologically acceptable acid-addition salt thereof or the steriosomer or optically active enantiomer thereof, excluding those compounds of the formula I in which:

(a) X is cl in 2-position, Y is H or Cl in 4-position, W, Q and $R^1$ are H, and $R^2$ and $R^3$ are methyl;

(b) X is Cl in 2-position, Y is Cl in 4-position, W, Q and $R^1$ are H, and $R^2$ and $R^3$ together with the carbon atom to which they are bound are cyclohexyl or 5-nonbornen-2-yl; or
(c) X is methoxy or Cl in 3-position, Y, W, Q and R¹ and H, and R² and R³ together with the carbon atom to which they are bound are 5-norbornen-2-yl.

2. A compound as claimed in claim 1, wherein at least one of the following features is fulfilled:

X is H, (C₁-C₄)-alkyl, phenyl, F, Cl, Br, I, CH₃OCH₂, C₂H₅OCH₂, CH₂=CHCH₂OCH₂, (C₁-C₄)-alkoxy, 3-N(CH₃)₂ or 3-CF₃, Y is H, CH₃, or OCH₃, or X and Y together in the 3,4-position represent a —(CH₂)₄—, —O—CH₂—O— or —CH=CH—CH=CH— chain, W is H, R¹ is (C₂-C₄)-alkyl, (C₂-C₅)-alkenyl, 2-propyn-1-yl, (C₃-C₆)-cycloalkyl, (C₁-C₄)-alkoxymethyl, (C₃-C₅)-alkenyloxymethyl, 2-propyn-1-yloxymethyl or

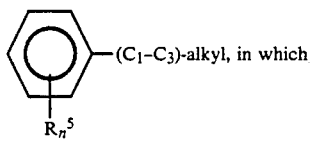

R⁵ is OCH₃, F or Cl and n is 0 or 1,

R² and R³ are (C₁-C₄)-alkyl or

R¹ and R³ or R² and R³, together with the carbon atom to which they are bound, represent (C₃-C₇)-cycloalkyl, C₇-bicycloalkyl or C₇-bicycloalkenyl whose C=C double bond is in other than the 1-position, each of which is unsubstituted or substituted by 1 or 2CH₃ and/or OCH₃, or (oxa-C₃-C₅)-cycloalkyl, and Q is H or CH₃ in the 4- or 5-position.

3. A compound as claimed in claim 1, wherein at least one of the following features is fulfilled:

X is H, CH₃, phenyl, F, Cl, Br, 3or 4-OCH₃ or 3-CH₃,

Y is H, CH₃, 3- or 4-Cl or 3- or 4-OCH₃, or

X and Y together in the 3,4-position represent a —CH=CH—CH=CH— chain,

W is H,

R¹ is (C₂-C₄)-alkyl (C₃-C₅)-alkenyl, 2-propyn-1-yl, benzyl, (C₁-C₄)-alkoxymethyl, or (C₃-C₄)-alkenyloxymethyl, R² and R³ are (C₁-C₄)-alkyl or R¹ and R³or R² and R³, together with the carbon atom to which they are bound, represent (C₃-C₇)-cycloalkyl, 2-norbornyl, norbornen-2-yl or (oxa-C₃-C₅)-cycloalkyl, and Q is H or CH₃ in the 4- or 5-position.

4. A medicament having an antimycotic or antidepressive action, containing an effective amount of a compound of the formula I as claimed in claim 1 together with a pharmaceutically acceptable carrier.

5. A process for treating mycosis, wherein an effective amount of a compound of the formula I as claimed in claim 1 is administered to a mammal together with pharmaceutically suitable excipients.

6. A process for treating depressive states, wherein an effective amount of a compound of the formula I as claimed in claim 1 is administered to a mammal together with pharmaceutically suitable excipients.

7. 1-(1-Aryl-2-hydroxyethyl)-imidazole of the formula I

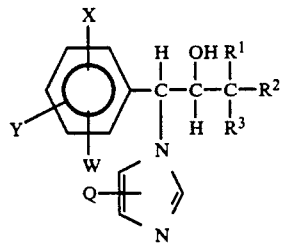

in which

X is (C₁-C₄)-alkyl, phenyl, F, Cl, Br, I, CF₃, (C₁-C₄)-alkoxy, (C₁-C₄)-alkylthio, (C₁-C₄)-alkoxymethyl, (C₃-C₅)-alkenyloxymethyl or —NR₂⁴, in which the radicals R⁴ are identical or different and are (C₁-C₄)-alkyl or, toegher with the nitrogen atom, a pyrrolidine, piperidine or morpholine radical, Y is H, (C₁-C₄)-alkyl, F, Cl, Br or (C₁-C₄)-alkoxy, or X and Y together in the 3,4-position represent a —(CH₂)ₗ-chain, where L=3 or 4, —OCH₂CH₂—, —O—CH₂O— or —CH=CH—CH=CH—, W is H, CH₃ or OCH₃, R¹ is (C₂-C₄)-alkyl, (C₂-C₅)-alkenyl, (C2l -C₅)-alkynyl, (C₃-C₈)-cycloalkyl, (C₄-C₈)-cycloalkenyl, (C₃-C₇)-cycloalkyl-CH₂, (C₄-C₇)-1-cycloalkenyl-CH₂, (C₁-C₄)-alkoxy, (C₁-C₄)-alkoxymethyl, (C₃-C₅)-alkenyloxymethyl or 2-propyn-1-yloxymethyl,

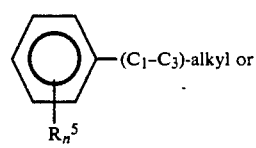

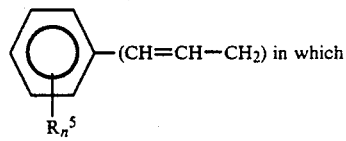

R⁵ is CH₃, C₂H₅, OCH₃, F, Cl, Br or CF₃, and n is 0, 1 or 2 and, in the case where R⁵ is CF₃, n is 1, R² is (C₁-C₄)-alkyl or (C₃-C₅)-alkenyl, R³ is (C₁-C₄)-alkyl or R¹ and R³ or R² and R³, together with the carbon atom to which they are bound are (C₃-C₇)-cycloalkyl, C₇-bicycloalkyl, (C₄-C₇)-cycloalkenyl or C₇-bicycloalkenyl which is in each case unsubstituted or substituted by 1-3 CH₃ and/or OCH₃ and/or Cl and in which, in cycloalkenyl and bicycloalkenyl radicals, the C=C double bond is in other than the 1-position, or (oxa-C₂-C₅)-cycloalkyl, and Q is H or CH₃ or C₂H₅ in the 4- and/or 5-position, the physiologically acceptable acid-addition salt thereof or the steroisomer or optically active enantiomer thereof.

* * * * *